US00PP08272P

United States Patent [19]

Jessel, Jr.

[11] Patent Number: Plant 8,272

[45] Date of Patent: Jun. 22, 1993

[54] CARNATION PLANT NAMED CFPC PRIMROSE

[75] Inventor: Walter H. Jessel, Jr., Salinas, Calif.

[73] Assignee: California Florida Plant Co., L.P., Salinas, Calif.

[21] Appl. No.: 757,838

[22] Filed: Sep. 11, 1991

[51] Int. Cl.[5] ..... A01H 5/00

[52] U.S. Cl. ..... Plt./70.4

[58] Field of Search ..... Plt./70.4, 73.3

[56] References Cited

U.S. PATENT DOCUMENTS

P.P. 7,911 7/1992 van Andel ..... Plt. 70.4

*Primary Examiner*—Howard J. Locker

*Attorney, Agent, or Firm*—Christie, Parker & Hale

[57] ABSTRACT

A new Carnation of clear light yellow coloration.

1 Drawing Sheet

SUMMARY OF THE INVENTION

The present invention relates to a new and distinct variety of Carnation plant which was originated by me in a controlled breeding program by my crossing as seed and pollen parents, two unnamed and unpatented seedlings of my creation. The varietal denomination of this new Carnation is 'CFPC Primrose'.

Among the novel combination of characteristics possessed by the new variety which distinguishes it are flowers of the attractive light yellow flower coloring which are produced on strong stems. Flowers of the new variety are produced as average-size, spray-type blooms which open fully without bursting the calyx and causing "splits".

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character. Although propagation by side shoot cuttings is described, other known methods of asexual reproduction may also be used to reproduce 'CFPC Primrose'.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Primrose.

Classification:

*Botanical.*—*Dianthus caryophyllus.*

*Commercial.*—Carnation, spray type.

Parentage:

*Female parent.*—Unnamed seedling (No. 8800470).

*Male parent.*—Unnamed seedling (No. 8700160).

PLANT

Height: About 40 inches.

Growing habit: Herbaceous, semi-upright, very vigorous, free breaking.

Blooming habit: Terminal as a spray.

Blooming season: Year round.

Rooting time: About 15–17 days.

Mutation prone: Does not appear to be.

Disease resistance: Unknown.

Temperature tolerance: Typical for Carnation.

Breaking action: Good.

FOLIAGE

Color:

*Upper side.*—Green.

*Lower side.*—Green.

Size: About 4½ inches long, about ¼ to ⅜ inch wide at base of plant.

Quantity: Numerous.

Shape: Lanceolate.

Texture: Smooth.

Ribs: Central, keeled.

Arrangement: Bi-lateral along stem.

Stem color: Green.

BUD

Shape: Oval.

Color: Green.

Length: About 1-inch.

Diameter: About ¾-inch.

CALYX

Number of sepals: About 6.

Length: About 1-inch.

Width: About ⅔-inch.

Color:

*Outside.*—Near to 138A.

*Inside.*—Near to 138D.

BLOOM

Shape: Round.
Size:
*Diameter average.—About* $1\frac{3}{4}$ to $2\frac{1}{8}$ inches.
*Depth average.*—About $1\frac{1}{4}$ inches.
Borne: Terminal as a spray.
Color:
*General tonality.*—Clear light yellow.
*Upper side.*—Near to from 5D to 5C.
*Lower side.*—Near to from 5B to 5C.
*Center.*—Near to from 5B to 5C.
*Outer petals.*—Near to from 5B to 5C.
Keeping quality: 10–14 days.
Fragrance: Very slight.

PETALS

Number: About 39 to 40.
Outer petals:
*Length.*—About 1-inch.
*Width.*—About $\frac{7}{8}$-inch.
Central Petals:
*Length.*—About $\frac{3}{4}$-inch.
*Width.*—About $\frac{1}{2}$-inch.
Texture: Smooth.
Form: Fan shaped.
Appearance: Shiny.

REPRODUCTIVE ORGANS

Stamens:
*Number.*—About 5 to 7.
*Arrangement.*—Around the ovary.
Anthers:
*Length.*—About $\frac{1}{8}$ to $\frac{3}{8}$-inch.
*Color.*—Tan.
Filaments:
*Length.*—About $\frac{1}{2}$ to $\frac{3}{4}$-inch.
*Color.*—Near to 158D.
Pistil:
*Number.*—About 3.
*Color.*—Near to from 157B to white.
*Length.*—About $\frac{3}{4}$ to $1\frac{1}{4}$ inches.
Stigma:
*Number.*—About 3.
*Color.*—White at maturity.
Ovary:
*Shape.*—Conical, ribbed.
*Color.*—Base — greenish white. Body — greenish yellow. Apex — tan.

I claim:

1. A new and distinct variety of Carnation plant, substantially as shown and described.

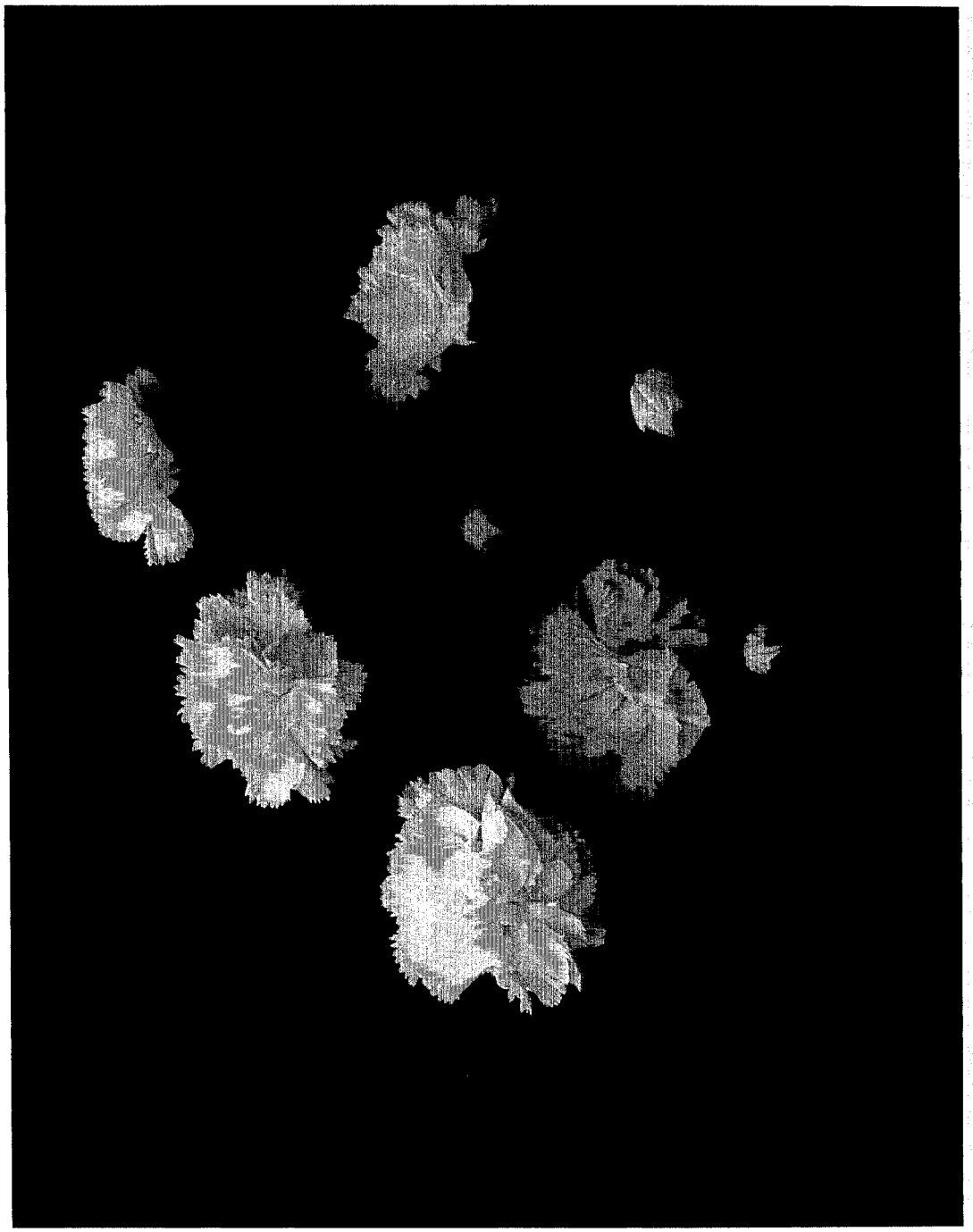

* * * * *